US00PP13040P2

(12) United States Plant Patent
Bradford

(10) Patent No.: US PP13,040 P2
(45) Date of Patent: Oct. 1, 2002

(54) PEACH TREE NAMED 'CANDY RED'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 09/733,415

(22) Filed: Dec. 11, 2000

(51) Int. Cl.[7] ..... A01H 5/00
(52) U.S. Cl. ..... Plt./197
(58) Field of Search ..... Plt./197

(56) References Cited

U.S. PATENT DOCUMENTS

PP7,066 P 12/1989 Bradford et al.

*Primary Examiner*—Bruce R. Campell
*Assistant Examiner*—Susan B. McCormick

(57) ABSTRACT

The present invention relates to a peach tree, botanical classification *Prunus persica* cultivar 'CANDY RED', and more particularly to a new and distinct variety broadly characterized by a medium size, vigorous, hardy, self-fertile, and medium productive tree. The fruit matures under the ecological conditions described approximately the second week in June, with first picking on Jun. 9, 2000. The fruit is uniformly large in size, very good in flavor, globose in shape, clingstone in type, firm in texture, yellow in flesh color, and mostly red in skin color. The variety was developed as a first generation cross using 'Crown Princess' (U.S. Plant Pat. No. 7,070) yellow flesh peach as the selected seed parent and an unnamed white flesh nectarine as the selected pollen parent.

1 Drawing Sheet

BOTANICAL CLASSIFICATION

*Prunus persica* cultivar 'CANDY RED'.

BACKGROUND OF THE VARIETY

In a continuing effort to improve the quality of shipping fruits, I, the inventor, typically hybridize a large number of nectarine, peach, plum, apricot, and cherry seedlings each year. The present invention relates to a new and distinct variety of peach tree, which has been denominated varietally as 'CANDY RED'. The present variety was hybridized by me in 1992, grown as a seedling on its own root in the greenhouse, and transplanted to a cultivated area of our experimental orchard at Bradford Farms near Le Grand, Calif. in Merced County (San Joaquin Valley). It was developed as a first generation cross using 'Crown Princess' (U.S. Plant Pat. No. 7,070) yellow flesh peach as the selected seed parent and an unnamed white flesh nectarine as the selected pollen parent. Subsequent to origination of the present variety of peach tree, I asexually reproduced it by budding and grafting, and such reproduction of plant and fruit characteristics were true to the original plant in all respects. The reproduction of the variety included the use of 'Nemaguard' (unpatented) rootstock, the standard of the stone fruit industry in central California, upon which the present variety was compatible and true to type.

The present variety is similar to its selected seed parent, 'Crown Princess' (U.S. Plant Pat No. 7,070) peach, by producing large clingstone peaches that are globose in shape, firm in texture, mostly red in skin color and yellow in flesh color, but is distinguished therefrom and an improvement thereon by having reniform instead of globose glands and by producing fruit that is subacidic instead of acidic in flavor and that ripens about six days later.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomologial characteristics of this new and distinct variety of peach tree, the following has been observed under the ecological conditions prevailing near Le Grand, Merced County (San Joaquin Valley), Calif., and was developed at the state of firm ripe on Jun. 12, 2000 on the original tree during its seventh growing season. All major color code designations are by reference to the Inter-Society Color Council, National Bureau of Standards. Common color names are also used occasionally.

TREE

Size: Medium, reaching and maintaining a height of 11' [3.35 m.] and a spread of 8' [2.44 m.] after seven growing seasons utilizing typical dormant pruning.

Vigor: Vigorous, responding typically to irrigation and fertilization. The varity grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Production: Medium productive, thinning sometimes necessary.

Fertility: Self-fertile.

Bearing: Some alternate bearing observed.

Trunk:

*Size.*—Medium, reaching a maximum diameter of 4.5" [114 mm.] after the seventh growing season.

*Texture.*—Rough.

*Bark color.*—Dark grayish yellowish brown [81. d.gy.yBr].

*Lenticels.*—Numerous. Color: Deep orange yellow [69. deep OY]. Typical Size: ¼" to 7/16" [6.4–11.1 mm.].

Branches:

*Size.*—Diameter of scaffold is 4½" [114 mm.] measured 12" above the crotch, typical of *Prunus persica*, and dependent upon cultural practices and climatic conditions.

*Texture.*—Smooth on 1st year wood, increasing roughness with age.

*Color.*—1st Year Wood Topside: Grayish red [19. gy.R]. 1st Year Wood Underside: Strong yellow green [117. s.YG]. Older Wood: Grayish brown [61. gy.Br].

*Lenticels.*—Numerous. Color: Moderate orange yellow [71. m.OY]. Typical Size: 1/16" to ¼" [1.6–6.4 mm.].

Leaves:

*Size.*—Large. Average Length: 6¼" [159 mm.]. Average Width: 1⅝" [41.3 mm.].

*Arrangement.*—Alternate.

*Thickness.*—Medium.

*Form.*—Elliptical.

*Apex.*—Acuminate.

*Base.*—Acute.

*Surface.*—Smooth.

*Color.*—Dorsal Surface: Dark olive green [126. d. OlG]. Ventral Surface: Moderate olive green [125. m.OlG].

*Margin.*—Finely serrate.

*Venation.*—Pinnately net veined.

*Petiole.*—Average Length: ½" [12.7 mm.]. Average Thickness: 1/16" [1.6 mm.]. Color: Strong yellow green [117. s.YG].

*Stipules.*—Numerous, usually 2 per leaf and up to 6 per growing tip. Average Length: ¼" [6.4 mm.].

*Glands.*—Numbers: 2 to 4 per leaf. Position: Most often oppositely positioned both on the petiole and the base of blade. Size: Medium. Form: Reniform. Color: Grayish reddish brown [46. gy.rBr].

*Leaf buds.*—Pointed.

Flower buds:

*Hardiness.*—Hardy, with respect to central California winters.

*Diameter.*—Typically ⅜" [9.5 mm.] 1 week before bloom.

*Length.*—Typically ¾" [19.1 mm.] 1 week before bloom.

*Form.*—Conic, not appressed.

*Surface.*—Pubescent.

*Color.*—Moderate purplish red [258. m.pR].

Flowers: Perfect, complete, perigynous, usually a single pistil, typically thirty or more stamens, five sepals and petal locations alternately positioned.

*Type.*—Showy.

*Average flower diameter.*—1¾" [44.5 mm.].

*Number of petals.*—Usually five, very few doubles.

*Petal shape.*—Circular.

*Petal margin.*—Slightly wavy.

*Average petal diameter.*—11/16" [17.5 mm.].

*Petal color.*—Pale purplish pink [252. p.pPk].

*Anther color.*—Very dark red [17. v.d.R] when first open.

*Stigma color.*—Light yellow [86. l.Y].

*Sepal color.*—Grayish purplish red [262. gy.pR].

*Sepal length.*—3/16" [4.8 mm.].

*Sepal width.*—3/16" [4.8 mm.].

*Average pistil length.*—¾" [19.1 mm.].

*Average stamen length.*—⅝" [15.9 mm.].

*Fragrance.*—Moderate when nectar is present.

*Blooming period.*—Medium compared with other varieties.

*Onset of bloom.*—One percent on Feb. 28, 2000.

*Duration of bloom.*—One to two weeks, dependent on ambient temperature.

FRUIT

Maturity when described: Firm ripe, Jun. 12, 2000.

Date of first picking: Jun. 9, 2000.

Date of last picking: Jun. 20, 2000.

Size: Uniform, large.

*Average diameter axially.*—2⅞" [73.0 mm.].

*Average diameter across suture plane.*—2¾" [69.9 mm.].

*Typical weight.*—7.3 ounces [206 grams].

Form: Uniform, slightly unsymmetrical, globose to slightly enlongated.

*Longitudinal section form.*—Round.

*Transverse section through diameter.*—Round.

Suture: An inconspicuous line toward the base becoming a shallow groove toward the apex, where it discontinues with a slight depression just beyond the pistil point.

Ventral surface: Strongly rounded, lipped toward the apex.

Lips: Somewhat unequal.

Cavity: Flaring, circular to slightly elongated in the suture plane, suture showing on one side, Pale yellow [89. p.Y] stem markings typical.

*Depth.*—½" [12.7 mm.].

*Breadth.*—1" [25.4 mm.].

Base: Truncate to somewhat cuneate.

Apex: Rounded.

Pistil point: Oblique, very short, usually depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Astringency.*—Slight to none.

*Tendency to crack.*—None observed.

*Color.*—Dark red [16. d.R] smoothly blending into a Dark reddish orange [38. d.rO] background color with some having Pale yellow [89. p.Y] areas where sun protected.

Down: Moderate, short, does not roll up when rubbed.

Flesh:

*Color.*—Brilliant yellow [83. brill.Y] to the stone with no red flecking or streaking.

*Surface of pit cavity.*—Brilliant yellow [83. brill.Y] fibers broken when twisted away from the stone.

*Amygdalin.*—Scarce.

*Juice.*—Abundant, rich.

*Texture.*—Firm, melting.

*Fibers.*—Abundant, fine.

*Ripens.*—Somewhat earliest along the lips.

*Flavor.*—Subacidic and sweet, ranging from 13 to 15 brix.

*Aroma.*—Slight.

*Eating quality.*—Very good.

STONE

Type: Clingstone.

Form: Oval.

Base: Straight.

Apex: Acute.

Sides: Equal.

Surface: Irregularly furrowed close to the apex and pitted from the base to above center.

Ridges: Jagged toward the base.
Color: Light yellowish brown [76. l.yBr].
Average pit wall thickness: ¼" [6.4 mm].
Average width: 1" [25.4 mm.].
Average length: 1⅜" [34.9 mm.].
Tendency to split: Slight.
Kernel:

*Form.*—Oval.
*Color.*—Strong yellow [84. s.Y] with Strong brown [55.s.Br] veins.
*Taste.*—Bitter.
*Viable.*—Yes.
*Average width.*—½" [12.7 mm.].
*Average length.*—⅝" [15.9 mm.].

Pellicle color: Strong brown [55. s.Br].
Amygdalin: Abundant.

USE

Market: Fresh and long distance shipping.
Keeping quality: Fruit quality observed to remain in good condition in excess of 21 days in standard cold room at 36° Fahrenheit [2° Celsius].
Resistance to insects: No unusual susceptibilities noted.
Resistance to diseases: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its selected seed parent, 'Crown Princess' (U.S. Plant Pat. No. 7,070) peach, by producing large clingstone peaches that are globose in shape, firm in texture, mostly red in skin color and yellow in flesh color, but is distinguished therefrom and an improvement thereon by having reniform instead of globose glands and by producing fruit that is subacidic instead of acidic in flavor and that ripens about six days later.

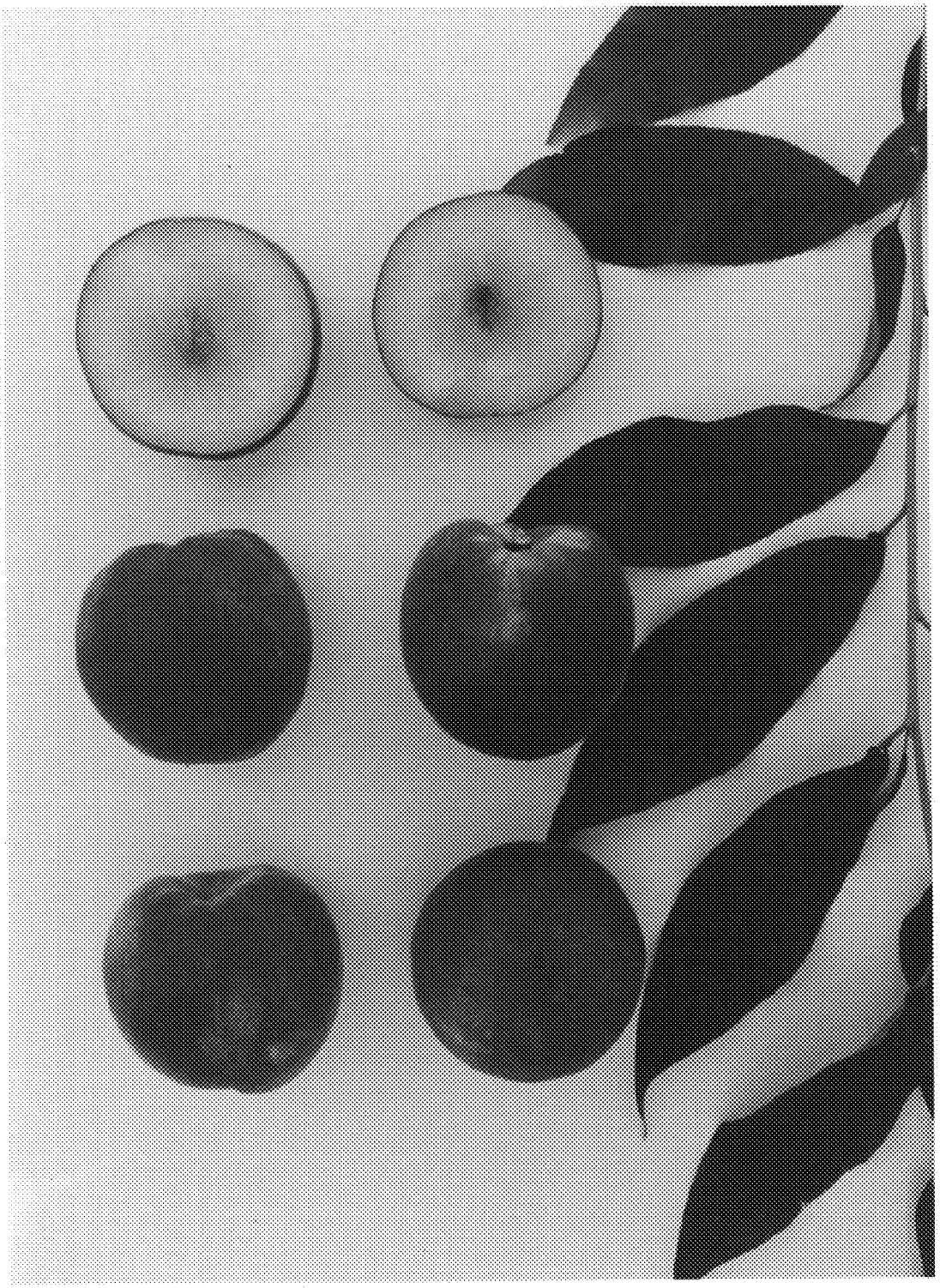

* * * * *